United States Patent [19]

Miyata et al.

[11] 4,271,070

[45] Jun. 2, 1981

[54] CHEMICALLY-MODIFIED FIBER COLLAGEN HEMOSTATIC AGENTS

[75] Inventors: Teruo Miyata, Tokyo, Japan; Albert L. Rubin; Kurt H. Stenzel, both of Englewood, N.J.

[73] Assignee: Cornell Research Foundation, Inc., Ithaca, N.Y.

[21] Appl. No.: 147,063

[22] Filed: May 5, 1980

[51] Int. Cl.³ .......................... C07G 7/00; C08L 89/06
[52] U.S. Cl. .................. 260/123.7; 106/155; 106/161; 128/156; 128/296; 128/334 R; 128/335.5; 128/325; 128/DIG. 8; 424/27; 424/28; 435/273
[58] Field of Search ..................... 260/123.7; 106/155, 106/161; 435/273

[56] References Cited

U.S. PATENT DOCUMENTS

| | | | |
|---|---|---|---|
| 2,973,302 | 2/1961 | Bloch | 435/273 |
| 3,034,852 | 5/1962 | Nishihara | 260/123.7 X |
| 3,071,477 | 1/1963 | Klevens | 426/59 |
| 3,114,593 | 12/1963 | Griset et al. | 264/103 X |
| 3,157,524 | 11/1964 | Artandi | 260/123.7 X |
| 3,314,861 | 4/1967 | Fujii | 435/897 X |
| 3,393,080 | 7/1968 | Erdi et al. | 260/123.7 X |
| 3,632,361 | 1/1972 | Battista | 260/123.7 X |
| 3,637,642 | 1/1972 | Fujii | 260/123.7 X |
| 3,649,347 | 3/1972 | Battista | 260/123.7 X |
| 3,898,129 | 8/1975 | Fujimoto et al. | 435/69 |
| 4,066,083 | 1/1978 | Ries | 128/335 |
| 4,140,537 | 2/1979 | Luck et al. | 260/123.7 |
| 4,215,200 | 7/1980 | Miyata et al. | 260/123.7 X |

OTHER PUBLICATIONS

J. of Am. Chem. Soc., vol. 74, 1952, Gustavson, pp. 4608–4611.
Chem. Abstracts, vol. 47, 1953, 901h–902a–c, Lennox et al.
Chem. Abstracts, vol. 47, 1953, 11787g–i, 11788d–i, 11789a, Cassel et al., Wiederman et al., Danby et al.
Trans-Amer. Soc. Artif. Int. Organs, Apr. 1976, Miyata et al., vol. XXII.
Chemical Reactions of Polymers, Fettes, 1965, pp. 384–386, 389–392.
Ann-Rev. of Biophysics & Bioengineering, vol. 3, 1974, pp. 231–253, Stenzel et al.
J. Clin. Inv., vol. 54, pp. 1480–1487, 1974, Brass et al.

*Primary Examiner*—Howard E. Schain
*Attorney, Agent, or Firm*—Edward J. Mahler

[57] ABSTRACT

Chemically-modified quaternary-structured fiber collagens of minimum molecular length, diameter and periodicity, and containing a relatively high positive electrostatic charge are claimed as hemostatic agents. Specific examples are guanidinated, esterified, and guanidinated-esterified collagen fibers of the type described.

10 Claims, No Drawings

CHEMICALLY-MODIFIED FIBER COLLAGEN HEMOSTATIC AGENTS

The U.S. Government has rights in this invention pursuant to Grant ROI-EYO1502 awarded by the Department of Health, Education and Welfare.

This invention relates to the production of chemically modified fiber collagen hemostatic agents. Specifically, the invention is concerned with specific fiber collagens in regularly staggered quaternary structure, further modified to contain a high positive electrostatic charge at physiologic pH or high isoelectric point. More particularly, the invention is concerned with hemostats prepared from such fiber collagen which has been guanidinated, esterified, and/or esterified-guanidinated.

In co-pending application Ser. No. 948,003, filed Oct. 2, 1978, now U.S. Pat. No. 4,215,200 we have described and claimed hemostatic agents consisting of chemically-modified, quanternary-structured, solubilized collagen of minimum molecular length, diameter and periodicity and having high positive electrostatic charges. In this invention collagen hemostats of the same characteristics are described and claimed, except that the collagen is not the enzyme-solubilized type, but rather fiber collagen, particularly that from animal tendon.

Native, undenatured fiber collagen (mature fiber collagen) is an aggregation of collagen molecules of various orders. The mature fiber is insoluble because of the covalent intermolecular crosslinks that cause it to become an infinite crosslinked network of its monomeric elements. Unlike atelocollagen, which has been enzyme-treated and solubilized, fiber collagen structure is unchanged and its fixed and predetermined configurations unaltered. It possesses the same basic tropocollagen quarter stagger molecular structure as soluble collagen, and already possesses many times the minimum polymeric requirements of molecular length of 7000 A°, minimum molecular diameter of 20 A° and periodicity of 700 A°, as set out by applicants for the preparation of an effective hemostatic agent. Examinations reveal that a fiber collagen particle obtained from insoluble collagen is many times the size of a collagen particle of atelocollagen.

Platelets play important roles in the initial stages of hemostasis. Platelets adhere to exposed subendethial connective tissue; additional platelets adhere to the layer of adherent platelets and form a platelet plug to be an effective barrier to further bleeding. The adherent platelets release clot-promoting factors and accelerate blood coagulation.

Native, unmodified collagen contains about 40 lysyl groups, 50 arginyl groups and 120 carboxyl groups per 1000 amino acid residues. Upon dissociation the carboxyl groups are negatively charged, while the lysyl and arginyl groups are positively charged.

It has been found that the guanidino groups of collagen play an important role in platelet-collagen interaction and that destruction of the guanidino groups on native type collagen fibrils (e.g. by reaction with hypobromite) abolishes platelet aggregating activity. Therefore, the introduction of additional guanidino groups into the molecule by guanidination of the lysyl groups greatly increases the opportunity for platelet aggregation, since the guanidinated surfaces being positively charged become attracted to the platelets which are negatively charged. Guanidination of the lysyl residue converts its $NH_2$ group to a homoarginyl residue which is similar to the arginyl residue in that both contain the guanidino group. The homoarginyl residue contains one additional carbon in the chain.

Collagen is a major component of connective tissue and it is well-known that platelets interact with collagen fiber by adhesion and aggregation. In other words, collagen is one of the important physiologic substances for the initiation of hemostasis.

Microcrystalline collagen (MCC) as a hemostat, has been described and its effects reported by recent investigators. For example, the use of MCC in the healing of bleeding bone has been reported as has the comparative effectiveness of MCC versus other agents such as purified gelatine solution and cellulose fiber. The present invention involves an improvement over simple microcrystalline collagen.

We have found that: (1) neither monomeric collagen nor esterified monomeric collagen is responsible for platelet aggregation; but that polymeric forms of collagen with regularly staggered quaternary structures are required to cause platelet aggregation; (2) critical minimum size of the collagen polymeric particle required to induce platelet aggregation is 7,000–10,000 A° in length; 20–40° in diameter, and at least 670–700 A° periodicity; (3) the arginyl residues of collagen are directly involved in collagen-platelet interaction; (4) platelet and fibrin depositions on guanidinated, methylated or methylated-guanidinated collagen surfaces were strongly enhanced when unmodified whole blood was exposed to such collagen surfaces. Fiber collagen, such as that prepared in accordance with this invention from animal tendon, possesses the polymeric requirements of criteria (1) and (2) above, and equally lends itself to the chemical modification of esterification and guanidination. These findings led to the conclusion that an effective collagen hemostatic agent can be prepared from esterified, guanidinated, or esterified-guanidinated fiber collagen aggregates with regularly staggered quaternary structure. The term quaternary structure refers to the association of tropocollagen into aggregates in which the monomers are structured parallel to each other but staggered by approximately one quarter of their length. We have prepared hemostatic agents from methylated, guanidinated and methylated-guanidinated regularly staggered quaternary fiber collagens in membrane, sponge, powder and gel forms and found that the new fiber collagen hemostatic agents were equally effective as the corresponding atelocollagen products of the earlier application mentioned above.

The above dimensions are the critical minima for the induction and maintenance of platelet aggregation. There appears to be no maximum except for the practicality of the handling of large size particles. The length of the fiber aggregate could be as high as 5 to 10 times the minimum and similarly, the diameter could be 3 to 5 times the minimum size. However, when making a gel form of the hemostat, a lesser molecular weight and diameter are preferred.

Native collagen is recovered in fiber form (not dissolved at all) by dispersion of the collagen in an aqueous medium and recovery by some means such as centrifuging, etc. Fiber collagen is usually recovered from animal tendon or hide as opposed to cartilege, membrane or bone source. Tendon, e.g., beef leg tendon, is desheathed, sliced and homogenized to separate individual tendon fibers in specialized "micro-cut" machines. Water is present during the machining of the tendon and the fibers become dispersed therein. The dispersion is repeatedly (2 or 3×) washed with dilute salt solution (5% NaCl) and the collagen fibers recovered by centrifuging. The fibers are washed with water to remove salt preparatory to enzyme treatment. The dispersion is treated with pancreatin, an enzyme which is very effective in dissolving elastin which encircles the fibers and binds them together. Other undesirable components, e.g., mucopolysaccharides and proteins, are also digested during this enzyme treatment which is carried out for about 24 hours at room temperature at pH of about 7-8 and enzyme concentration of 0.5 wt % based on the weight of dry collagen. After recovering the collagen fibers by centrifuge, the fibers are washed with dilute aqueous salt solution and finally with water after which they are defatted if necessary. The product is recovered from the defatting solvent, dried in air, powdered and swollen to about 1% collagen dispersions.

Hide collagen is worked up on the same manner as tendon collagen to produce fibers therefrom, but in doing so it is recommended that the hair side and flesh side be cut away and only the corium layer used.

Fiber collagen possesses high tensile strength and its high degree of natural crosslinking makes it easier to purify without degradation, particularly, during enzyme treatment wherein a milder acting enzyme such as pancreatin may be used.

The hemostatic effect is the result of enhancing the interaction between platelets and arginyl residues of modified collagen which is brought about indirectly by increasing the net positive charge of collagen or, directly, by increasing the guanidino groups, or by a combination of the two. The increased net positive electrostatic charge is brought about mainly by converting the carboxyl group of the fiber collagen to an ester by reaction with an alcohol or other ester-forming compound. The increase of guanidino groups is accomplished by reacting the $NH_2$ group of the lysyl residues with chemical substances capable of converting amino to guanidino groups.

When speaking of high electrostatic charge or high isoelectric point it is meant that the chemically modified fiber collagen aggregate has, (at physiologic pH, i.e. about 6.8 to 7.4) a higher positive charge or higher isoelectric point than the unmodified fiber collagen. For example, unmodified fiber collagen has an isoelectric point (pI) of 9.0; but when methylated it has a pI of 10.5; and when methylated and guanidinated its pI exceeds 12.0. During esterification about 85% of the carboxyl groups of the molecule become methylated, and about 50% of the lysyl groups become converted to guanidino groups during the guanidination reaction.

Preparation of Fiber

The preparation of the collagen fiber is illustrated in detail in the following description. Adult bovine achilles tendon collagen is cleaned by removing fat tissue and dirt materials and chopped in a meat grinder utilizing the largest plate hole. Chopped tendon is passed through a Stephan's microcutter with a cutting aperture of 10 mm. Feeding of tendon to the machine is helped by adding water to the tendon in the machine hopper to the extent of 10 to 20 times the weight of tendon. If tendon particles larger than 2 mm remain after the first microcutter treatment, a second cutting is carried out with same cutting aperture (10 mm). A third microcutter treatment is performed with a cutting aperture of 1.0 mm. Tendon collagen is well disintegrated into fine fiber and no collagen mass remains after these microcutter treatments.

The disintegrated collagen is next treated with pancreatin (enzyme: collagen=0.5~1.5:100 on dry wt. basis) at pH 6.5~8.0 for 24 hours at 20° C. (room temperature). Pancreatin digests proteinaceous substances, e.g. elastin, in the tendon collagen which bind the fibers into bundles. The removal of such substances facilitates the separation of individual collagen fibrils in the acidic dispersion. Most preferable conditions for pancreatin treatment are: ratio of pancreatin to collagen 1:100 on dry wt. basis; pH 7.4; temperature 20° C., and incubation period 25 hours. To adjust the pH a buffer solution of M/15 phosphate is recommended. In order to depress microorganism growth the addition of a bectericide, e.g., 0.1 wt. % of methylparaben is preferably added to the enzyme solution. The ratio of enzyme solution to dry collagen is recommended to be 20:1 (solution: collagen). Other proteolytic enzymes having optimum pH in the neutral region such as trypsin, papain, ficin may be used in place of pancreatin.

Pancreatin-treated tendon is centrifuged to collect the collagen after which it is washed with water, and again centrifuged. Washed collagen is added to water (collagen:water—0.5~1.5:100 on dry wt. basis), and homogenized well in a Waring blender to disperse the fibrils. Lactic acid is added to the dispersion to adjust the pH to 2.5 to 4.0, preferably about 3.0, and the dispersion is again well blended. Addition of 0.1 wt. % methylparaben to the acidic dispersion as a preservative is recommended. Blending of the acidic dispersion separates the collagen fibrils and makes a viscous gel consisting of evenly dispersed fibrils. Heat is produced during the blending, therefore the dispersion should be kept under 30° C. e.g. by cooling in an ice bath. Temperatures over 40° C. induce denaturation of the collagen and should be avoided. Collagen concentration in the acid dispersion is preferably kept in the area of 1.0 wt. %.

CROSSLINKING

Since fiber collagen is already highly crosslinked, especially when the starting material is adult tendon collagen, little or no additional crosslinking is necessary. The need for additional crosslinking is preferably to be avoided by choosing the preferred source of collagen material. The collagen hemostat used in the human body should be resorbed as soon as the blood becomes coagulated. Excessive crosslinking of the collagen delays the resorption. Should any additional crosslinking become necessary ultraviolet irradiation or aldehyde treatment may be used, preferably the latter.

UV irradiation consists of treating the collagen contained in a quartz flask in the presence of nitrogen in an irradiation chamber equipped with four 15-watt germicidal lamps radiating primarily at 2537 A°. The flask is situated in an ice bucket in the center of the chamber. The treatment is carried out for about 2 hours after which the collagen is removed, washed with water and recovered.

When treating with an aldehyde, formaldehyde is preferred, since formaldehyde crosslinks are less stable in the body and resorption is quicker than with the higher aldehydes, e.g., glutaraldehyde. Conditions recommended for formaldehyde treatment are: formaldehyde 1.0%, pH 8.5; (0.02 M $Na_2HPO_4$ buffer), 20° C., for about 2 min.

Crosslinking, if performed, takes place prior to any esterification or guanidination of the collagen fiber.

Esterification

The fiber collagen prepared as illustrated above was esterified in accordance with the following procedure:

Methylation-Acidified methanol containing 0.1 M HCl was dehydrated by intermittent stirring with excess annhydrous $Na_2SO_4$. Collagen in whatever form, gel or powder, was methylated in the acidified methanol for a period of about 7 days at room temperature in a tightly sealed vessel. After methylation, the collagen product was dried in a vacuum and pulverized in a Wiley Mill with 100 mesh seive. From the dry powdered collagen gels thereof were prepared by mixing with water and homogenizing in a Waring blender for subsequent treatment and use.

In place of methanol in the esterification reaction other alcohols may be employed, preferably other water-soluble aliphatic alcohols such as ethanol, propanol, etc.

Guanidination

The following procedure was employed to effect the guanidation of the fiber collagen aggregate: 100 grams of dry fiber collagen was suspended in 1 liter of water and the pH adjusted to 9.5 by the addition of NaOH. Eighty (80) grams of 1-guanyl-3, 5-dimethylpyrazole nitrate were dissolved in 1 liter of water and the pH again adjusted to about 9.5. The collagen dispersion and the reagent were mixed and allowed to stand for 7 days at about 4° C. with intermittent stirring. The collagen quaternary structure remained stable during the reaction. After guanidination the collagen was washed with water and collected by centrifugation.

The invention is more clearly understood from the following examples which are meant to be typical and in no way restrictive of the invention:

EXAMPLE 1

Fiber Collagen Gel

A supply of fiber collagen gel which is used in subsequent reactions to make the desired hemostat was prepared in accordance with the method outlined in the preceding section entitled "Preparation of Fiber".

EXAMPLE 2.

Methylated Fiber Collagen Hemostat

Viscous acidic fiber collagen gel dispersion was dehydrated with methanol containing sodium sulfate dessicant with intermittent stirring. About 100 grams of dehydrated fiber collagen was esterified in two liters of anydr. methanol containing 0.1 N NCl for 7 days at room temperature. The methylated product was recovered (dried, swollen in dil. HCl and homogenized to 1.0% dispersion) and divided into portions. One portion was dried in a vacuum and pulverized in a Wiley Mill with a 100 mesh to make a methylated fiber collagen hemostat in powder form. Another portion was poured in a flat vessel to a depth of 1 cm. and air-dried to a membrane type hemostat. Still another portion was likewise poured but freeze-dried to make a hemostat of the sponge sheet type.

EXAMPLE 3

Guanidinated Fiber Collagen Hemostat

About 100 grams of fiber collagen gel dispersion was suspended in one liter of water, and NaOH added to adjust the pH to 9.5. 1-Guanyl-3,5-dimethylpyrazol nitrate (80 gms.) was dissolved in one liter of water and the pH likewise adjusted to 9.5. Collagen suspension and the reagent were mixed together and allowed to stand for 7 days at about 4° C. with intermittent stirring. After guanidination the product was collected by centrifugation and washed three times with water. The guanidinated fiber collagen was dispersed in dil. HCl (pH 3) to a 1% viscous gel. As in Example 2 the product was divided into portions and hemostats in powder, membrane and sponge sheet form were prepared.

EXAMPLE 4

Methylated-Guanidinated Fiber Collagen Hemostat

100 Grams of Methylated fiber collagen gel (1.0% dispersion) were prepared by the method of Example 2 above and suspended in 1 liter of water at pH of 9.5. The guanidinating reagent was likewise prepared in accordance with the method of Example 3 above. Methylated fiber collagen suspension and reagent were mixed together and allowed to stand for 7 days at 4° C. and pH 9.5. The reaction mass was stirred intermittently. After the reaction was complete the guanidinated-methylated fiber collagen product was recovered by centrifugation and washed with water a number of times. A 1.0% viscous gel thereof was prepared by dispersing the procuct in dilute HCl solution, pH 3.0. Once again, in addition to the gel product, hemostats in powder, membrane and sponge sheet form were prepared as above.

The methylated and methylated-guanidinated fiber collagen products prepared as above were tested as hemostats in the wounds of a dog. Bleeding was arrested, time of bleeding reduced, and healing of tissue with absorption of the hemostat practically complete in 7-8 days. In all cases foreign body reaction was absent and no inflammatory reaction appeared. The powder form of the above hemostats was markedly superior to a commercially available powder collagen hemostat. The products demonstrated results comparable to that previously obtained by the applicants with corresponding methylated, guanidinated collagen hemostats made from enzyme-solubilized atelocollagen.

The hemostatic agent of this invention is particularly applicable to the control of bleeding from surfaces, especially large surfaces, rather than control of blood flow from large vessels. For example, the hemostatic agent is useful on (a) cut or severed bone, (b) a severed organ, e.g. spleen, liver or kidney which has been cut surgically or traumatically, (c) the central nervous system where small blood vessels predominate, (d) prosthetic surgery, (e) oozing surfaces resulting from the surgical removal of necrotic tissue, (f) cosmetic surgery and (g) any surfaces with oozing of blood from one or more small sources, e.g. facial cuts.

The hemostatic agent may be applied in a variety of forms, e.g. as a powder directly to the surface; as a styptic in pencil form; as a gel, membrane, sponge sheet, or in fabric form. The amount of agent employed varies with the extent of the bleeding surface and severity of the blood flow. Sufficient agent is applied to effect the desired control.

Having described the invention as above in specific detail, what is claimed is:

1. An improved collagen hemostatic agent comprising native crosslinked fiber collagen of regularly staggered quaternary structure having a minimum molecular length of 7000 A°, a minimum molecular diameter of 20 A°, a minimum periodicity of 670–700 A°, and whose residual lysyl and carboxyl groups have been subjected respectively to at least one reaction selected from the group consisting of guanidination, esterification and guanidination-esterification to greatly enhance the net positive electrostatic charge of the fiber collagen.

2. A hemostatic agent of claim 1 in which the collagen is native animal tendon collagen.

3. A hemostatic agent of claim 1 in which the fiber collagen lysyl residues have been guanidinated.

4. A hemostatic agent of claim 1 in which the fiber collagen carboxyl residues have been esterified.

5. A hemostatic agent of claim 1 in which the fiber collagen lysyl and carboxyl residues have been guanidinated and esterified respectively.

6. A hemostatic agent of claim 1 in which the fiber collagen is in sponge sheet form.

7. A hemostatic agent of claim 1 in which the fiber collagen is in powder form.

8. A method of preparing an improved fiber collagen hemostatic agent which comprises forming an acidic dispersion of native fiber collagen characterized by regularly staggered quaternary structure having a minimum molecular length of 7,000 A, a minimum molecular diameter of 20 A, and a minimum periodicity of 670–700 A, subjecting the dispersion to at least one chemical reaction selected from the group consisting of esterification, guanidination, and esterification-guanidination, whereby the net positive electrostatic charge of the fiber collagen is greatly enhanced, and recovering the chemically-modified fiber collagen from the reaction mixture.

9. A method according to claim 8 in which the fiber collagen dispersion is made from animal tendon.

10. A method according to claim 8 in which the acidic dispersion is dissolved in water and the solution brought to an alkaline pH before chemical reaction.

* * * * *